United States Patent [19]

Swenson

[11] Plant 4,928

[45] Nov. 9, 1982

[54] GRAPEVINE

[76] Inventor: Elmer Swenson, Rte. 2, Box 118, Osceola, Wis. 54020

[21] Appl. No.: 233,685

[22] Filed: Feb. 11, 1981

[51] Int. Cl.[3] ..... A01H 5/03
[52] U.S. Cl. ..... Plt./47
[58] Field of Search ..... Plt./47

[56] References Cited

U.S. PATENT DOCUMENTS

P.P. 3,686 2/1975 Triplett ..... Plt./47

*Primary Examiner*—Robert E. Bagwill
*Attorney, Agent, or Firm*—Merchant & Gould

[57] ABSTRACT

A grapevine which exhibits winter hardiness down to −39° F. in northern Wisconsin, with grapes of very low acidity and high sugar content, no labrusca flavor or aroma, and producing a good wine similar to a light to medium burgundy.

3 Drawing Figures

ORIGIN AND REPRODUCTION

The present invention relates to a new and distinct variety of grapevine which was produced by me as a result of an ongoing grape breeding program at my vineyard and nursery located in Polk County, near Osceola, in northern Wisconsin. The present variety is characterized by excellent winter hardiness and usefulness as a wine grape, having low acidity and high sugar content, with no foxiness or labrusca flavor or aroma.

For some 40 years, I have been growing a large number of grapevines at my above-noted nursery and vineyard in northern Wisconsin with a breeding program directed to the production of grapevines having the desirable winter hardiness for northern states and commercially useful as wind and/or table grapes.

By way of background, it is noted that there have been very few desirable commercial grape varieties for growing in the harsh northern climate of Minnesota and Wisconsin, and similar northern states. Although this northern region has a summer thermal accumulation similar to that of the best grape growing areas of the world, the low winter temperatures have generally prevented development of vineyards in this region because of the lack of suitably hardy grape varieties.

Current vineyard cultural practices in the noted northern region generally involve early fall pruning, after which the vines are removed from trellises and laid upon the ground and covered for wintering. In the spring, the vines are uncovered and re-trellised, all of which involves considerable labor costs, which are generally prohibitive and make it quite difficult for northern vineyards in such climates to operate profitably. Accordingly, for grapevines to be of high commercial value to vineyards in such northern regions, such as Minnesota and Wisconsin, it has become nearly essential that the varieties be hardy enough to remain on the trellises throughout the winter months without removal and winter covering. The present variety has this desirable characteristic.

This new variety of grapevine was selected by me for its combination of excellent winter hardiness and usefulness as a wine grape, producing a wine similar to a medium to light burgundy.

The present variety is a result of my above-noted breeding program, in which my varietal selections are designated by number with the prefix ES. This variety is a selecting seedling resulting from my cross of ES283 (ES114×Seyval) × ES193 (Minnesota 78×Seneca). I have identified the present variety as ES2-3-21 and selected the name "St. Croix" therefor.

I have reproduced the present variety by means of cuttings, and have carefully observed, the variety for several years. The continual observation and testing of the present variety has convinced me that it is a new and improved cultivar of grapevine, as indicated by the following unique combination of outstanding qualities which distinguish this variety from all other varieties of grapevine known to me.

SUMMARY OF CHARACTERISTICS

The unique combination of characteristics of the present variety ES-2-3-21, named "St. Croix", are as follows:

1. *Winter hardiness.*—The present variety has excellent winter hardiness for northern states, whereby the vines may remain on trellises throughout the winter without covering. More specifically, this variety has survived on trellises with a winter temperature of −39° Fahrenheit with no apparent injury to the vines or buds thereon and with no winter covering. Such survival has been at my vineyard and nursery located near Osceola, in Polk County, in northern Wisconsin. My observations indicate this variety to be as winter hardy as the Beta variety.

2. *Low acidity.*—The present variety has also produced grapes of relatively low acidity, a desirable attribute for wine grapes. For the year 1979, a poor year for grapes in northern Wisconsin with relatively low heat summation, the present variety tested 1.4 percent for acidity, as compared to 1.5 percent for the Foch variety. In 1980, this variety produced grapes with an acidity of 0.7 percent.

3. *High sugar content.*—This cultivar also has the characteristic of relatively high sugar content, another desirable attribute for wine grapes. In 1979, the present variety tested a Brix of 20.0°, as compared to 20.5° for the Foch variety. In 1980, this variety tested a Brix of 18.1° on Sept. 7, 1980.

4. *Flavor and color.*—Foxiness or labrusca flavor or aroma is a generally undesirable characteristic for wine grapes, yet is typical of previous varieties having good winter hardiness. The present variety produces grapes with no foxy or labrusca flavor. Wine produced from the present variety has been described by Mr. David Bailly of Alexis Bailly Vineyard as follows:

"The color was very good, medium to light burgundy. The smell and taste were light and pleasant, generally described as a light viniferous style."

The variety also produces grapes having a desirable dark blue-purple color imparting a medium to light burgundy color to wine produced therefrom.

ASEXUAL REPRODUCTION

The present variety has been asexually reproduced by me by means of vine cuttings at my nursery and vineyard in Polk County, near Osceola, Wis. Such asexual reproduction confirms that the characteristics and qualities stated herein for this variety are true to form and consistent through succeeding propagation.

DETAILED DESCRIPTION

The accompanying drawings comprise photographs showing characteristics of this new variety. The photographs were taken of specimens of the variety growing in my aforementioned vineyard and nursery near Osceola, Wis., and the color photographs depict color features as true as reasonably possible.

FIG. 1 is a color photograph showing the form and growth of a mature vine of the present variety.

FIG. 2 is a color photograph showing the mature summer leaf form for typical leaves of the variety.

FIG. 3 is a color photograph showing typical fruit clusters of the present variety.

The following is a detailed description or specification of the pomological characteristics of my new variety, with color terminology or references in accordance with the Royal Horticultural Society Color Chart. Where dimensions, sizes, colors and other characteristics are given, it is to be understood that the same are approximations of averages as they appear under conditions prevailing in my vineyard near Osceola, Wis.

Vine:

*Growth habit.*—Not upright but has a trailing growth habit suitable for the Geneva Double Curtain trellis style. Vigorous.

*Trunk.*—Thick and sheds bark in long strips in Riparia fashion. Color brown. Needs support.

*Canes.*—Average length is 3.5 meters. Spacing between nodes is 10.0 centimeters. Tendrils are intermittent and tend to slip every third node.

Foliage:

*Leaves.*—Top sinuses deep and narrow. Lower sinuses very shallow. Petiolar sinus wide and U-shaped with petiole nearly at right angles to the leaf. Mature leaf color close to Yellow-Green Group 147B. Fresh leaves under 4.0 centimeters have a slight coppper tint and close to Yellow-Green Group 152A. Mature leaf size is approximately 7.2 inches wide and 8.3 inches long.

Grapes:

*Maturity.*—Early mid-season. Late August to mid-September at my noted vineyard. Trellis methods, pruning and weather are factors. Similar to Foch.

*Size of berry.*—Natural 1.1 centimeter average.

*Shape of berry.*—Spherical.

*Ripening.*—Usually 3 weeks from turning color to maturity depending on weather. Berries begin ripening unevenly on cluster but even at maturity. Fruit holds well on vine with no shriveling.

*Cluster.*—Similar to Beta in outline and appearance. Cluster is slightly cylindrical to conical. Usually single-shouldered. Medium to compact. Average length is 14 centimeters with largest cluster about 20 centimeters in length. Three clusters per shoot common. Average cluster stem is 3 centimeters. Cluster weight is 7.8 oz. average. Approximately fifty-five (55) berries per cluster.

*Seeds.*—2.8 average seeds per berry. Seeds are dark brown color.

*Pulp.*—Tender and juicy, not stringy. Fresh pulp is close to Green Group 145D.

*Juice color.*—Free run juice color is close to Red Purple Group 59A.

*Sugar and acid.*—Brix of 20.0° (1979); Brix of 18.1° and acid of 0.7% on Sept. 7, 1980.

*Color of berry.*—Berry on cluster is close to Blue Group 103A.

Other characteristics: Perfect flowers, self-pollinating. Appears to be as winter hardy as Beta. Very resistant to downy mildew and black rot at vineyard near Osceola, Wis.

I claim:

1. A new and distinct variety of grapevine, substantially as shown and described herein, characterized particularly as to novelty by the unique combination of winter hardiness down to −39° F. in northern Wisconsin, with grapes of very low acidity, high sugar content, no labrusca flavor or aroma, and producing a good wine similar to a light to medium burgundy.

* * * * *

FIG. 1
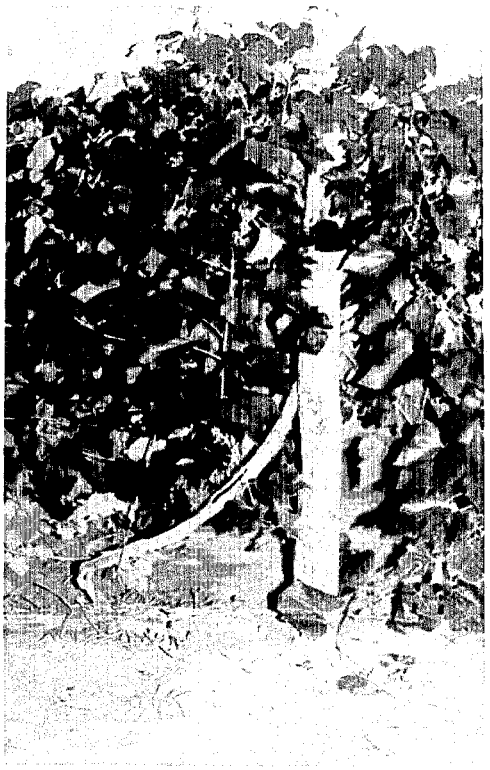
FIG. 3
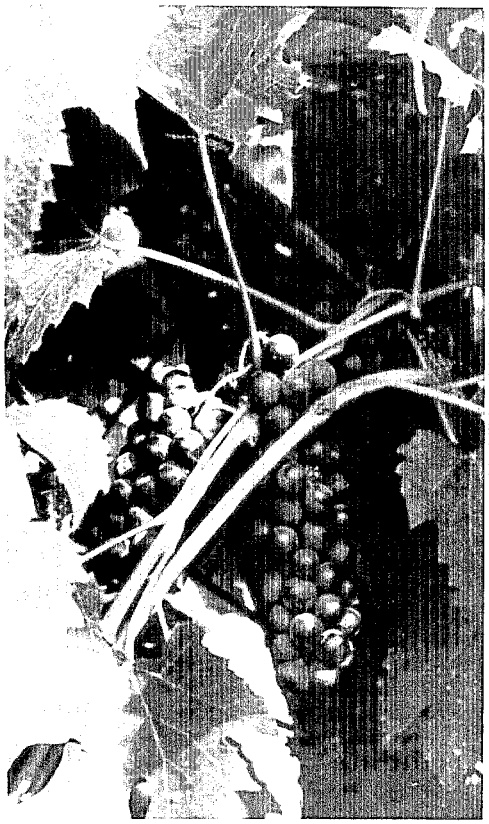
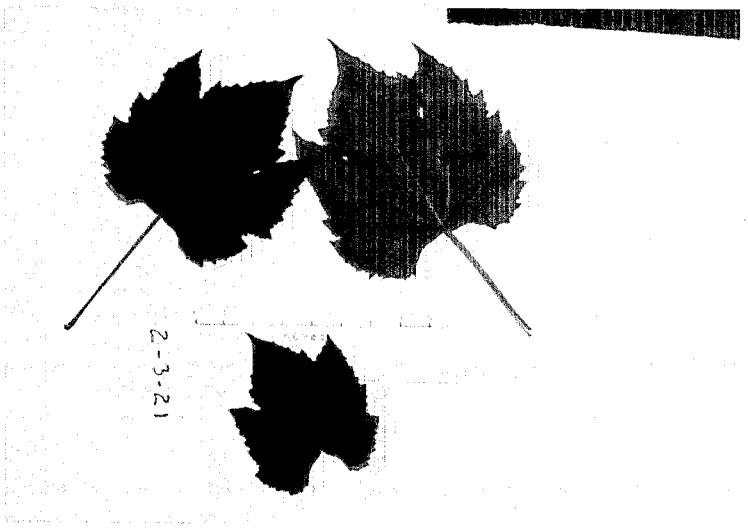
FIG. 2